United States Patent [19]

Charley

[11] Patent Number: 5,292,507
[45] Date of Patent: Mar. 8, 1994

[54] METHOD OF USING POLYSACCHARIDES TO STABILIZE MICROORGANISMS FOR INOCULATING PLANT SEEDS

[75] Inventor: Robert Charley, Oakville, Canada

[73] Assignee: Imperial Oil Limited, Canada

[21] Appl. No.: 945,437

[22] Filed: Sep. 14, 1992

Related U.S. Application Data

[63] Continuation of Ser. No. 563,800, Aug. 6, 1990, abandoned, which is a continuation of Ser. No. 385,926, Jul. 27, 1989, abandoned, which is a continuation of Ser. No. 892,078, Aug. 1, 1986, abandoned.

[51] Int. Cl.$^5$ .......................... C12N 1/04; C12N 1/00; C05F 11/08
[52] U.S. Cl. ........................ 424/93 K; 71/6; 71/7; 424/93 N; 424/93 Q; 435/243; 435/252.2; 435/252.5; 435/253.3; 435/260; 504/100
[58] Field of Search ................. 424/93; 435/41, 42, 435/243, 252.1, 252.2, 254, 260, 93 K, 93 N, 93 Q, 252.5, 253.3; 71/6, 7; 47/57.6, 58; 504/100

[56] References Cited

U.S. PATENT DOCUMENTS

| | | | |
|---|---|---|---|
| 2,908,614 | 10/1959 | Muggleton et al. | 167/78 |
| 2,995,867 | 8/1961 | Burton | 47/1 |
| 3,168,796 | 2/1965 | Scott et al. | 47/1 |
| 3,600,830 | 8/1971 | Hamrin | 47/57.6 |
| 3,688,437 | 9/1972 | Hamrin | 47/57.6 |
| 3,898,132 | 8/1975 | Hettrick | 195/65 |
| 4,155,737 | 5/1979 | Dommergues et al. | 71/7 |
| 4,434,231 | 8/1981 | Jung | 435/253 |
| 4,588,584 | 5/1986 | Lumsden et al. | 424/93 |

FOREIGN PATENT DOCUMENTS

| | | |
|---|---|---|
| 0551717 | of 1986 | Australia. |
| 0017565 | 10/1980 | European Pat. Off. . |
| 0083267 | 7/1983 | European Pat. Off. . |
| 0097459 | 1/1984 | European Pat. Off. . |
| 0196593 | of 1986 | European Pat. Off. . |
| 2303080 | of 1976 | France. |
| 2469861 | 6/1981 | France. |
| 2501229 | of 1982 | France. |
| 8502972 | 7/1985 | PCT Int'l Appl. . |
| 1526317 | of 1978 | United Kingdom. |
| 2080669 | of 1982 | United Kingdom. |

OTHER PUBLICATIONS

Jung, et al., *Plant and Seed*, 65:219-231 (1982).
Fravel, et al., *Phytopathology*, 75:774-777 (1985).
Takata, et al., *J. of Solid-Phase Biochem.*, 2(3):225-236 (1977).
Kierstan, M., and Bucke, C., *Biotech. and Bioengineering* 21:387-397 (1977).
Bashan, Y., *Applied and Environmental Microbiology*, 51(5): 1089-1098 (1986).
Hansen et al. (1984) Appl. Environ. Microbiol. 47(4): 704-709.
Kearney el al., Appl. Environ. Microbio 56(16): 3112-3116 (1990)

*Primary Examiner*—David M. Naff
*Attorney, Agent, or Firm*—Edward F. Sherer

[57] ABSTRACT

Soluble, non-crosslinked polysaccharides are used to stabilize microorganisms for use as inoculants in agriculture. Preferably, the polysaccharide is alginate and plant seeds are inoculated. A solution of the polysaccharide and a suspension of the microorganism are mixed to form a composition containing about 0.005% to about 10% of the polysaccharide. The composition can be stored for one week or more before use and the composition may be dried.

12 Claims, No Drawings

METHOD OF USING POLYSACCHARIDES TO STABILIZE MICROORGANISMS FOR INOCULATING PLANT SEEDS

This application is a continuation of application Ser. No. 07/563,800, filed Aug. 6, 1990, which is a continuation of application Ser. No. 07/385,926, filed Jul. 27, 1989, which is a continuation of application Ser. No. 06/892,078, filed Aug. 1, 1986, all now abandoned.

FIELD OF THE INVENTION

The invention pertains to a method for stabilizing bacterial cells for extended periods of time. This stabilization is achieved through the formation of a slurry containing the bacterial cells, and non-cross-linked agents such as polysaccharides. The invention further pertains to a composition of matter containing non-crosslinked sodium alginate and microorganisms in suspension. The invention also pertains to the above composition which additionally contains oils in emulsions. Additionally, the invention pertains to the composition and use a dry powder which could be used to coat seeds. The invention further pertains to the use of such dry powders as microbial inoculants in agriculture. The invention also pertains to the use of sodium alginate and microorganisms in solution, dried to a powder and used to coat seeds directly or when suspended in oil.

BACKGROUND ART

The use of microbial inoculants (such as Rhizobium) has long been known to increase crop yields. The utility of this approach has been limited by the availability of compositions capable of both affixing the microbial cells to the seed and maintaining the viability of the microbial inoculant. Burton, J. C. (U.S. Pat. No. 2,995,867) discloses the possibility of using water soluble gums such as methylcellulose as a seed coating. Through the use of such coatings, it is possible to keep microbial cells alive and effective for over two weeks.

The success of this work spurred others to attempt to identify alternate compositions which might be capable of maintaining bacterial viability for longer periods of time. A method was disclosed by Hamrin, B.S.A. (U.S. Pat. No. 3,688,437), which involved the use of seed coatings comprising a gelatin-calcium alginate foam. Dommergues, Y. R., et al. (U.S. Pat. No. 4,155,737) disclosed the possibility of embedding the microbial inoculant in a polyacrylamide seed coating.

The possibility of stabilizing bacterial cells in a microbial inoculant through the use of a polysaccharide matrix was shown by Mugnier, J., et al. (French Patent 2,469,861). This patent discloses the ability to stabilize a suspension of bacterial cells by embedding them in an alginate gel. The gel disclosed in this patent is formed by the addition of calcium chloride to a solution containing a suspension of bacterial cells and sodium alginate. The addition of calcium chloride results in the precipitation and crosslinking of the previously soluble sodium alginate mixture.

A similar alginate composition is disclosed by Jung, G. (European Patent 17,565 and U.S. Pat. No. 4,434,231). These patents disclose the possibility of crosslinking or precipitating solutions of sodium alginate that contain suspensions of bacterial cells. The Jung patents disclose the use of calcium sulfate to convert a sodium alginate suspension into a gel. This crosslinking reaction can be delayed through the addition of sodium phosphate to the suspension. Bacterial cells treated in this manner remained viable for greater than 60 days. These patents further disclose the use of such embedded microorganisms as microbial inoculants in agriculture. Although the ease of formation of cross-linked alginate gels commended their use as an embedding matrix for a microbial inoculant, such matrices were found to be inferior to embedding matrices of xanthan gums in that embedding matrices composed of xanthan gums were found to release microorganisms into the soil more readily than matrices composed of alginates. (Jung, G., et al., *Plant and Soil*, 65:219–231 (1982)).

Jung, et al. (European patent no. 83267) disclose compositions containing microbial cells and polymeric gels which may be dried and used to inoculate plant seeds. The patent further discloses the use of a cross-linked alginate suspension of microbial cells as a microbial inoculant.

One concern reflected in the prior art is that suitable embedding agents should provide an environment strong enough to resist external abrasion and adverse forces yet be pliable enough to allow release of internal components and permit breakdown of the matrix at the appropriate time. Two different methods have been disclosed in order to accomplish this goal. Redenbaugh, M. K., et al. (P.C.T. Publication W085/02972) disclosed the use of crosslinked alginate-bacterial cell suspensions which are surrounded by an external membrane as a microbial inoculant. Fravel, D. R., et al. (*Phytopathology*, 75:774–777 (1985)) disclosed the use of crosslinked alginate-bacterial cell suspensions which contain clays or other materials, added as bulking agents. The process disclosed by Fravel, et al produces solid pellets of relatively uniform size.

Thus, the prior art teaches the value of pre-inoculating seeds with microbial suspensions in order to enhance their germination and growth. A wide variety of different embedding matrices have been disclosed in the prior art. Especially significant are matrix compositions which employ crosslinked or precipitated alginates or very thick, gum-like compositions. Such compositions have been successful in sustaining bacterial cell viability for extended periods of time, while simultaneously possessing the desired properties of rigidity and support. The preparation of gels, however, requires additional steps and both gels and gums involve handling difficulties.

SUMMARY OF THE INVENTION

The present invention relates to an improved process for maintaining cell viability and cellular integrity under conditions (temperature, pH, enzymatic reactions, etc) under which cell viability and integrity would normally deteriorate. The invention is useful in the formation of microbial inoculants in agriculture.

The invention utilizes the properties of a liquid system wherein the cells are protected from environmental conditions, but freely accessible to substrates and co-factors, which may be added at any time to the system. The liquid system described by the invention may have varying degrees of fluidity, but does not have semi-solid, viscous, gel- or gum-like properties.

The invention is based on the discovery that non-crosslinked polysaccharide solutions stabilize the viability of non-dormant microbial cells. Such solutions can also, in accord with the present invention, be used to preserve dormant microbial cells for subsequent use.

In detail, the invention pertains to a method for maintaining the viability of a microorganism which comprises: maintaining a suspension of the microorganism in a free-flowing composition which comprises a water dispersible, substantially soluble, non-crosslinked polysaccharide.

Additionally, the invention pertains to a method for inoculating a plant seed with a microorganism which comprises: providing to the plant seed a free flowing composition which comprises (i) a suspension of the microorganism and (ii) a water dispersible, substantially soluble, non-crosslinked polysaccharide.

The invention is also directed to a method for maintaining the viability of a microorganism which comprises: drying a free-flowing composition, the composition comprising a suspension of the micoorganism and a water dispersable, substantially soluble, non-crosslinked polysaccharide to form a dried composition.

The invention is further directed to a method for inoculating a plant seed with a microorganism which comprises:
(a) drying a free-flowing composition, the composition comprising a suspension of the microorganism and a water dispersible, substantially soluble, non-crosslinked polysaccharide, to form a dried composition, and
(b) providing the dried composition (a) to the plant seed.

DESCRIPTION OF THE PREFERRED EMBODIMENTS

The present invention relates to suspensions containing polysaccharides, and the use of such suspensions as a means of stabilizing or preserving microbial cells.

The invention further relates to drying a solution which comprises a non-crosslinked polysaccharide, and a microorganism to produce a powder and using the powder obtained after drying either directly or when dispersed in oil.

As used herein, the term "microbial cells" refers to any of a wide variety of microorganisms. Examples of such microorganisms are Pseudomonas, Serratia, Arthrobacter, Azospirillum, Rhizobium and Bacillus, but the invention can be used to maintain the viability of any microorganism which has a beneficial effect on the growth, emergence, yield, etc. of plants.

The term "polysaccharide," as used in this invention is meant to refer both to polysaccharides which must be externally added to the suspension of microbial cells, and to polysaccharides produced directly by a microorganism under appropriate culture conditions, such as for example by permitting cultures of microorganisms to enter growth limiting conditions (e.g. nitrogen exhaustion) with an excess of carbon, or energy source. (Sutherland, I. W., Microbial Polysaccharides and Polysaccharases, (Berkeley, Gooday, and Ellwood, eds.) Acad. Press NY (1979)). An example of a polysaccharide included in the invention is the polysaccharide obtained from algae. Such polysaccharides are collectively referred to as "alginates." The invention is specifically directed to the use of polysaccharides which are substantially soluble in an aqueous solution. Examples of such polysaccharides are alginates, celluloses, or starches. The soluble polysaccharides of the present invention are further restricted to those which are non-crosslinked.

As used in this invention, a polysaccharide is considered to be "non-crosslinked" if the polysaccharide is either free of intermolecular crosslinks, or if the degree of crosslinking is of such minor character so as to permit the polysaccharide to remain soluble in an aqueous solution. The concentration of polysaccharide in these solutions is described as its concentration relative to that of the total volume of the solution (i.e. as a weight-/volume percentage). Unless otherwise indicated the alginate-microorganism mixtures of the present invention are prepared by dissolving alginates in water and then adding the alginate solution to a culture broth. The degree of crosslinking is less than 10%, preferably less than 5%.

The present invention relates to the use of "water dispersible," "free flowing" compositions. These terms are meant to refer to compositions which have low viscosity, and are pourable. These terms are specifically intended to exclude compositions which are solids, gels or gums at ambient (4° C.–30° C.) temperatures.

As used herein, the terms "dried" or "drying" is intended to describe the removal of water. Any means capable of achieving the removal of water may be employed. Suitable techniques including air drying, spray drying, lyophilizing, etc. are well known in the art.

As used herein, the term "oil" refers to any of a large class of compounds which are soluble in hydrophobic solvents such as ether or alcohol, but are substantially insoluble in water. The oils suitable for use in the present invention are liquids at ambient temperatures. Examples of suitable oils are: Mineral oil, or vegetable oils such as soya oil, canola oil, corn oil, etc.

As mentioned above, an oil is substantially insoluble in water. Thus a water/oil mixture will tend, upon storage, to spontaneously separate (on the basis of density) into two substantially pure solutions, one of which contains the oil and the second of which contains the water. Although the present invention can be practiced with a water/oil mixture, it is preferable to add an "emulsifier" or "emulsifying agent" to the mixture. An emulsifier is a substance which is capable of enhancing the dispersion of the aqueous phase into the oil. Emulsifiers are disclosed by Huettinger, R., (Seif., Oele, Fette, Wachse, 109:455–479 (1983)). Examples of suitable emulsifying agents are Arlacel 83 TM, Arlacel 186 TM and Tween 81. Arlacel TM is manufactured by ICI Chemical Corp.

The present invention provides a means for stabilizing the viability of microbial cells and may be used to preserve microorganisms for a wide variety of applications. In particular the present invention may be used to maintain viability of microorganisms in inoculants for agricultural and industrial applications. According to the invention cells may be stabilized to provide a suitable storage period for one week or more and then applied easily to seeds in the form of a liquid, free-flowing coating to produce a variety of effects including enhancement of emergence, growth and yield. The applied microorganisms may function in diverse manners to produce the desired response and include members of the genera Rhizobium, Pseudomonas, Bacillus, Arthrobacter, Serratia and Azospirillum.

The invention can be performed using a large number of possible non-crosslinked polysaccharides, such as starch, or xanthan gum, however it is preferable to use alginate polysaccharides. Although the invention can be practiced using polysaccharide solutions which range from 0.01–20%, it is preferable to use polysaccharides solutions of between 0.5–2.5%, with about 1.0–2.0% being most preferable for alginate.

To produce the polysaccharide-bacterial cell suspensions of the invention, aliquots of a fresh, healthy culture of cells containing a cell concentration high enough to provide any desired biological or industrial effect, but not so high as to negatively interfere with such effect, and preferably between 1-50 grams of cells (dry weight) per liter, are mixed with equal aliquots of sterile solutions containing a soluble polysaccharide to produce a solution containing about 0.005% to about 10% by weight of the polysaccharide. Bacterial cultures treated in this manner may then be stored at any temperature wherein the bacteria remain viable, such as, e.g., between 4°-30° C. The degree of bacterial stabilization has been found to be independent of the sample storage temperature.

The polysaccharide solution may contain nutrients or growth factors such as, for example, sugars, amino acids, proteins, salts, etc. In addition, the polysaccharide solutions may contain osmoregulatory agents, such as buffers, which may be required in order to practice the invention.

In one embodiment of the invention, the bacterial cells are suspended in a polysaccharide solution which may then be applied to seeds, by any of a variety of means, such as, for example, dipping, spray drying, etc. Such techniques are disclosed by Cull, S. W., et al. (European Patent 97,459); Mugnier, J., et al. (French Patent 2,469,861); Jung, G. (U.S. Pat. No. 4,434,231); and Redenbaugh M. K., et al. (PCT No. WO85/02972).

In a preferred embodiment of the invention, the bacterial cells are suspended in a non-crosslinked polysaccharide solution and then incorporated into an oil emulsion. This composition may then be used as an agricultural inoculant, for example, by diluting it with water and using it as a liquid spray or by coating it directly onto seeds. The polysaccharide/cell solution may alternatively be dried to a powder to provide successful storage either alone or, preferably, in combination with agrichemicals. This powder may be applied directly to seeds, or may be dissolved in water or dispersed in oil to produce a liquid which can be sprayed onto seeds.

The previously cited techniques applying polysaccharide/bacterial cell suspensions to seeds can be readily adapted by one of ordinary skill in the art so as to enable their application to the compositions of the present invention. It is, however, preferable to dry the suspensions at 30° C. by blowing air over their surfaces. This is preferably accomplished by placing the suspension in an incubator and blowing sterile, filtered air across the surface of the suspension. The dried composition may then be coated onto seeds by mixing.

Having now generally described this invention, the same will be better understood by reference to certain specific examples which are included herein for purposes of illustration only and are not intended to be limiting of the invention, unless specified.

EXAMPLE 1

Growth of Microbial Strains

*Rhizobium japonicum* cultures where maintained on YEM agar plates (10 g mannitol; 0.5 g (Difco) yeast extract; 0.5 g $K_2HPO_4$; 0.2 g $MgSO_4.7H_2O$; 0.1 g NaCl; 20 g agar; water to 1L. 100 ml liquid cultures were obtained by inoculating 100 ml of medium A (10 g sucrose; 0.5 g (Veeprex B800) yeast autolysate; 0.22 g $K_2HPO_4$; 0.1 g $MgSO_4.0.7H_2O$; 0.04 g $CaCl_2$; 0.02 g $FeCl_3$; water to 1L) with a single colony from a YEM agar plate. The liquid cultures were incubated at 30° C. for 7 days on a orbital shaker at 140 RPM. One liter cultures were obtained by transferring a fresh 100 ml culture into 1L of medium A and incubating for 5-7 days at 30° C. on an orbital shaker at 140 RPM.

Unless otherwise indicated, all other cultures were maintained on PAF agar plates (38 g (Gibco) Pseudomonas agar F; 10 g glycerol; 20 g agar; water to 1L) liquid cultures were obtained by inoculation of TSB (30 g (Gibco) tryptic soy broth; water to 1L) with a single colony from a PAF agar plate and incubating at 30° C. for 48 hours on an orbital shaker at 140 RPM.

EXAMPLE 2

Effect of Temperature on Stability of *Rhizobium japonicum*

*Rhizobium japonicum* USDA 138 was grown as described in Example 1. 50 ml of fresh culture medium was mixed with an equal amount of sterile solutions of 1% and 2% non-crosslinked sodium alginate to produce samples having 0.5% or 1% alginate. Samples containing a final alginate concentration of 1% were stored at 4° C., room temperature, and 30° C. The sample containing 0.5% alginate was stored at room temperature. Periodically, the mixtures were well agitated and samples removed for viable cell culture counts. The result of this experiment is shown in Table 1. This experiment demonstrated that the stability of *R. japonicum* cells in an alginate slurry was essentially unaffected by storage temperature.

TABLE 1

| Sample | Log viable count/mL | | | | | |
|---|---|---|---|---|---|---|
| | to | 1 wk | 4 wks | 10 wks | 21 wks | 26 wks |
| 1%; 4° C. | 8.84 | 8.45 | 7.99 | 9.06 | 9.59 | — |
| 1%; RT | 9.61 | 8.93 | 9.86 | 9.44 | 8.64 | — |
| 1%; 30° C. | 9.42 | 8.70 | 8.85 | 9.06 | 8.53 | 8.17 |
| 0.5%; RT | 10.42 | 9.68 | 9.62 | 9.29 | 8.86 | — |

EXAMPLE 3

Effect of Polysaccharide on Stability of *Rhizonbium japonicum*

*Rhizobium japonicum* USDA 138 was grown as described in Example 1. Samples of the liquid cultures were removed and mixed with the non-crosslinked polysaccharides shown in Table 2. Mixtures were stored at room temperature and sampled periodically for viable cell counts following vigorous agitation. This experiment showed that a wide variety of soluble polysacchrides could be used to sustain the viability of bacterial cells.

TABLE 2

| Sample | Log viable count/ML | | | | |
|---|---|---|---|---|---|
| | to | 1 wk | 4 wks | 10 wks | 30 wks |
| 2.5% Dextran | 7.76 | 10.48 | 9.14 | 8.78 | 8.00 |
| 0.25% Waterlok B100 | 7.92 | 9.78 | 8.37 | 8.52 | 6.60 |
| 3.5 Corn starch | 7.83 | 9.56 | 9.93 | 10.54 | 9.29 |
| 0.5% Carboxymethyl-cellulose | 7.88 | 9.33 | 9.26 | 10.84 | 8.18 |
| 0.5% Gum ghatti | 7.63 | 8.51 | 8.65 | 8.36 | 8.31 |
| 0.5% Xanthan gum | 8.19 | 9.72 | 9.39 | 9.13 | 8.79 |
| 1% Gum arabic | 7.77 | 9.26 | 9.47 | 10.21 | 7.89 |
| 0.5% Gelatin | 7.73 | 9.42 | 9.59 | 9.04 | — |
| 0.5% Alginate/0.5 M sorbitol | 7.88 | 9.55 | 9.03 | 10.99 | 9.23 |
| 0.5% Alginate/0.5 M sucrose | 7.36 | 7.97 | 9.94 | 9.00 | 9.15 |
| 0.5% Alginate/0.5% saline | 7.62 | 8.43 | 7.44 | — | 0 |
| 0.5% Alginate/0.5% yeast | 7.81 | 8.49 | 7.29 | 5.31 | 0 |

TABLE 2-continued

| Sample | Log viable count/ML | | | | |
|---|---|---|---|---|---|
| | t0 | 1 wk | 4 wks | 10 wks | 30 wks |
| autolysate | | | | | |
| 0.5% Alginate/0.5% activated charcoal | 7.79 | 9.68 | 8.87 | 8.14 | 8.03 |
| 0.5% Alginate/14% beet molasses | 8.01 | 8.51 | 6.61 | 5.82 | 0 |
| 1.5% Carboxymethyl-cellulose | 7.61 | 9.44 | 9.49 | 9.26 | 7.56 |
| 2.5% Alginate | 7.71 | 8.74 | 9.08 | — | — |
| 0.5% Alginate | 7.74 | 9.38 | 9.00 | 8.31 | 7.85 |
| 0.05% Alginate | 7.77 | 8.87 | 9.34 | 8.33 | — |
| 0.5% Alginate + 0.15% B-cyclodextrin | 7.71 | 8.97 | 9.24 | 8.61 | 7.94 |

EXAMPLE 4

Stability of Pseudomonas and Bacillus Cultures in Alginate Slurries 50 ml of fresh healthy cultures of *Pseudomonas fluorescens* 17-34, *Pseudomonas putida* 1-104, *Pseudomonas sp* 55-14, *Pseudomonas sp.* 67-4, *Bacillus sp.* 86-64 and *Pseudomonas putida* G2-8 were grown as described in Example 1 and mixed with equal aliquots of sterile 1% non-crosslinked alginate solutions. The mixtures were stored at room temperature and periodically agitated and sampled for viable cell counts. The results of this experiment are shown in Table 3. This experiment shows that 1% alginate slurries are successful in stabilizing a variety of bacterial strains.

TABLE 3

| Organism | Log viable count/ML | | | | | |
|---|---|---|---|---|---|---|
| | T0 | 1 wk | 4 wks | 8 wks | 10 wks | 34 wks |
| P. fluorescens 17-34 | 11.88 | 11.83 | 11.02 | 8.16 | 7.43 | 7.00 |
| P. putida 1-104 | 10.19 | 11.33 | 10.32 | 8.27 | 7.45 | 7.40 |
| Pseudomonas sp. 55-14 | 11.80 | 11.08 | 9.62 | 8.76 | 6.61 | 7.22 |
| Pseudomonas sp. 67-4 | 11.85 | 12.04 | 10.27 | 8.22 | 7.21 | 8.29 |
| Bacillus sp. 86-64 | 9.49 | 9.86 | 9.36 | 7.79 | 7.03 | 8.20 |
| P. putida G2-8 | 10.41 | 11.73 | 11.48 | 8.26 | 7.25 | 8.26 |

EXAMPLE 5

Effect of Storage in Sealed Vials on the Stability of Pseudomonas and Bacillus Strains in Alginate Solutions Aliquots of fresh healthy cultures of *Pseudomonas fluorescens* 17-34, *Pseudomonas putida* 1-104, *Pseudomonas sp.* 55-14, *Pseudomonas sp.* 67-4, *Bacillus sp.* 86-64 and *Pseudomonas putida* G-28 were grown as described in Example 1. Aliquots were mixed with equal volumes of a sterile 1% non-crosslinked alginate solution and dispensed into sterile 2.2 ml glass vials. The vials were completely filled and tightly capped, and were then stored at 30° C. or room temperature. Periodically samples were agitated and viable cell counts were determined. The results of this experiment are shown in Table 4. This experiment shows that adequate gaseous exchange is required in order to maintain cell viability in alginate solutions.

TABLE 4

| Organism | Storage Temperature | Log viable count/ML | | | | |
|---|---|---|---|---|---|---|
| | | T0 | 1 wk | 2 wks | 3 wks | 5 wks |
| P. fluorescens 17-34 | RT | 12.03 | 9.79 | 5.32 | 2.71 | 3.79 |
| 17-34 | 30° C. | 11.72 | 9.97 | 6.37 | 5.76 | 3.97 |
| P. putida 1-104 | RT | 11.44 | — | 9.20 | 6.20 | 3.62 |
| | 30° C. | 11.45 | — | 5.32 | 4.32 | 3.86 |
| Pseudomonas sp. 55-14 | RT | 11.80 | 11.64 | 5.70 | 4.72 | 3.97 |
| | 30° C. | 11.88 | 11.67 | 8.15 | 1.79 | 0 |
| Pseudomonas sp. 67-4 | RT | 12.60 | — | 3.34 | 3.46 | 3.32 |
| | 30° C. | 12.84 | — | 3.46 | 3.75 | 3.62 |
| Bacillus sp. 56-64 | RT | 9.32 | 9.46 | 9.17 | 5.72 | 5.35 |
| | 30° C. | 9.32 | 9.57 | 5.71 | 4.67 | 2.98 |
| P. putida G2-8 | RT | 12.41 | — | 5.46 | 5.45 | 5.31 |
| | 30° C. | 12.45 | — | 5.62 | 4.25 | 3.32 |

EXAMPLE 6

Survival of *Rhizobium japonicum* 138 in Alginate Solutions and Oil Emulsions in Bulk and When Coated onto Soyabeans

*Rhizobium japonicum* cultures were grown as described in Example 1. 250 ml of a fresh, healthy *R. Japonicum* culture was mixed with 250 ml of a sterile 1% non-crosslinked alginate solution. This mixture was designated solution A. 100 ml aliquots of solution A were removed and mixed with Food and Cosmetic Blue Dye #1 (final dye concentration=1.0%) (to form mixture B) or with Food and Cosmetic Blue Dye #1 (final dye concentration=1.0%) and Tween 81 (final concentration=2.0%) (to form mixture C). The mixtures were i) added to the alginate prior to sterilization (blue dye) and ii) sterilized independently and added to the final mixture (Tween).

4 ml aliquots of the above mixtures were then dispensed into sterile 4.5 ml glass vials. In addition, 0.8 ml aliquots of solution C were dispensed into vials containing 3.2 ml of sterile mineral oil (to form solution D). All vials were then tightly sealed and stored at room temperature. Vials were removed periodically and agitated vigorously prior to sampling for viable cell count analysis. Table 5 shows the effect of time on the viability of cells in mixtures A–D.

Additionally, at the time of preparation 0.4 ml samples of mixtures A–D were used to coat 10 g samples of soybean seeds. Aliquots of coated seeds were removed periodically to allow the number of viable cells surviving on the seed coating to be determined. FIG. 6 shows the effect of time on the viability of cells of mixtures A–D coated onto soybeans. While viability of *R. japonicum* was maintained in all the mixtures, the alginate/cell/oil emulsion is preferred since this composition facilitated seed coating and enhanced the flowability of the seeds. Successful survival on the seed coat also shows that the mixtures can be employed as seed inoculants.

TABLE 5

| | To | 3 wks | 7 wks | 10 wks | 16 wks | 37 wks |
|---|---|---|---|---|---|---|
| A | 10.40 | 9.58 | 9.33 | 9.26 | 8.11 | 7.75 |
| B | 10.93 | 10.93 | 9.81 | 9.39 | 7.71 | 7.99 |
| C | 9.65 | 8.46 | 9.20 | 8.75 | 6.30 | 6.31 |
| D | 10.52 | 10.62 | 10.18 | 9.92 | 8.70 | 8.20 |

TABLE 6

| | \multicolumn{6}{c}{Log viable count/seed (stored at room temperature)} |
|---|---|---|---|---|---|
| | To | 2 h | 4 h | 6 h | 24 h | 1 wk |
| A | 6.22 | 5.87 | 5.55 | 4.62 | 4.64 | 3.27 |
| B | 6.61 | 6.35 | 6.43 | 4.66 | 5.24 | 3.65 |
| C | 6.01 | 5.47 | 5.12 | 4.81 | 4.48 | 2.73 |
| D | 5.39 | 5.66 | 5.35 | 4.25 | 5.24 | 3.79 |

EXAMPLE 7

Effect of Polysaccharide on Stability of Bacillus sp. 86-64

Bacillus sp. 86-64 was grown as described in Example 1. 50 ml aliquots of a fresh, healthy culture were mixed with an equal amount of a solution containing: 6% alginate; 4% alginate; 2% alginate; 4% alginate and 1.8% saline; 4% alginate and 1.0M sucrose; 4% alginate and 1% activated charcoal; 4% alginate and 1.5% cyclodextrin; 4% alginate and 2% corn starch; 4% alginate and 2% glycerol; 4% alginate and 1% gelatin; or 4% dextran, to form the following mixtures: Mixture A—culture medium+3% alginate; Mixture B—culture medium+2% alginate; Mixture C—culture medium+1% alginate; Mixture D—culture medium+2% alginate+0.9% saline; Mixture E—culture medium+2% alginate+0.5M sucrose; Mixture F—culture medium+2% alginate+0.5% activated charcoal; Mixture G—culture medium+2% alginate+0.75% cyclodextrin; Mixture H—culture medium+2% alginate+1% corn starch; Mixture I—culture medium+2% alginate+1% glycerol; Mixture J—culture medium+2% alginate+0.5% gelatin; Mixture K—culture medium+2% dextran. All alginate solutions contained only non-crosslinked alginates. The mixtures were stored at room temperature and sampled periodically to determine the viable cell count. The result, given in Table 7, shows that a variety of polysaccharide mixtures and alginate together with various adjuvants enhanced the stability of Bacillus sp. 86-64.

TABLE 7

| | \multicolumn{4}{c}{Log viable count/ml} |
|---|---|---|---|---|
| | to | 4 wks | 10 wks | 29 wks |
| A | 8.94 | 8.91 | 7.52 | 7.28 |
| B | 8.68 | 8.38 | 7.52 | 7.51 |
| C | 8.61 | 8.06 | 6.09 | 7.98 |
| D | 8.75 | 8.78 | 7.33 | 6.50 |
| E | 8.71 | 8.77 | 7.52 | 5.59 |
| F | 8.60 | 9.26 | 7.90 | 7.23 |
| G | 8.64 | 8.13 | 6.45 | 6.51 |
| H | 8.69 | 8.56 | 7.12 | 7.63 |
| I | 8.69 | 8.75 | 7.89 | 7.60 |
| J | 8.80 | 8.09 | 7.59 | 7.24 |

TABLE 7-continued

| | \multicolumn{4}{c}{Log viable count/ml} |
|---|---|---|---|---|
| | to | 4 wks | 10 wks | 29 wks |
| K | 8.73 | 8.32 | 6.43 | 6.55 |

EXAMPLE 8

Viability of P. fluorescens 17-34, Pseudomonas sp. 55-14 and Bacillus sp. 84-64 in Alqinate Mixtures and Alginate/Oil Emulsions 50 ml aliquots of fresh healthy cultures of *Pseudomonas fluorescens* 17-34, Pseudomonas sp 55-14 and Bacillus sp. 86-64 were grown as described in Example 1. Cultures were grown in 250 ml Erlenmeyer flasks. 50 ml of the culture broth were mixed with equal aliquots of the following non-crosslinked polysaccharide compositions: (A) 4% alginate; (B) 4% alginate plus 2% <Food and Cosmetic Blue Dye #1; and (C) 4% alginate plus 2% (final concentration) Food and Cosmetic Blue Dye #1 plus 2% activated charcoal. Additionally, 10 ml culture aliquots were mixed with 10 ml aliquots of the above alginate/dye mixture and either (D) 80 ml sterile soya oil; (E) 78 ml sterile soya oil plus 2 ml Arlacel 83 TM or (F) 78 ml sterile soya oil plus 2 ml Arlacel 186 TM. All flasks were stoppered with cotton wool bungs and stored at room temperature. At various times, the mixtures were well agitated and a viable cell count determination was made.

The results, shown in table 8, indicates that incorporation of the alginate/cell solutions into an oil emulsion enhanced cell survival.

TABLE 8

| | \multicolumn{9}{c}{Log viable count/ml} |
|---|---|---|---|---|---|---|---|---|---|
| | \multicolumn{3}{c}{Bacillus sp. 86-64} | \multicolumn{3}{c}{Pseudomonas sp. 55-14} | \multicolumn{3}{c}{P. fluorescens 17-34} |
| | To | 1 mo | 6 mo | To | 1 mo | 6 mo | To | 1 mo | 6 mo |
| A | 7.16 | 7.99 | 8.00 | 9.96 | 8.10 | 7.23 | 11.05 | 7.81 | 8.01 |
| B | 7.86 | 8.10 | 7.35 | 11.33 | 8.80 | 7.41 | 11.22 | 8.34 | 7.97 |
| C | 7.62 | 8.32 | 6.71 | 11.06 | 8.61 | 7.68 | 11.04 | 8.35 | 7.93 |
| D | 8.78 | 11.33 | 11.81 | 8.35 | 11.92 | 10.96 | 8.53 | 11.94 | 11.57 |
| E | 8.51 | 8.33 | 12.04 | 8.25 | 11.32 | 11.36 | 8.57 | 11.69 | 11.62 |
| F | 8.46 | — | 9.76 | 8.47 | 12.40 | 9.51 | 8.41 | 11.25 | 11.31 |

EXAMPLE 9

Survival of Rhizobacteria Coated onto Soyabeans and Canola (rape) Seed Using an Alginate/Oil Emulsion System Cultures of rhizobacterial strains were prepared as described in Example 1

Fresh, healthy cultures were mixed with equal volumes of sterile 4% alginate. Aliquots of the culture/alginate solutions were then incorporated into emulsions with either canola or soya oil in a ratio of 30% aqueous: 68% oil: 2% emulsifier (Tween 81) to produce mixtures which were then coated onto canola seeds or soyabeans using 60 uL of mixture/10 g of seed or 75uL of mixture/25 g of beans. Seed samples were removed periodically to determine the viable cell count. The results, presented in Table 9, show the efficacy of the formulation as a microbial seed inoculant delivery system.

TABLE 9

| | | \multicolumn{5}{c}{Log viable count/seed} |
|---|---|---|---|---|---|---|
| | | To | 2 h | 24 h | 48 h | 96 h |
| Coated | *Azospirillum* sp. | 2.94 | 2.58 | 1.98 | 2.14 | — |

TABLE 9-continued

|  |  | \multicolumn{5}{c}{Log viable count/seed} |
|  |  | To | 2 h | 24 h | 48 h | 96 h |
| --- | --- | --- | --- | --- | --- | --- |
| onto | Arthrobacter sp. 44-9 | 2.55 | 2.55 | 2.22 | 2.35 | — |
| canola | P. fluorescens 34-13 | 3.15 | 3.10 | 2.91 | 3.20 | — |
| seeds in canola emulsion |  |  |  |  |  |  |
| Coated | Bacillus sp. 86-64 | 5.31 | 4.92 | 4.56 | — | 3.81 |
| onto | Azospirillum sp. | 4.06 | 3.43 | 3.03 | — | 2.21 |
| soyabeans | P. putida 57-10 | 4.95 | 4.41 | 3.95 | — | 3.33 |
| in soya | P. fluorescens G20-18 | 4.31 | 3.95 | 3.43 | — | 3.38 |
| oil emulsion | Serratia liquifaciens 1-102 | 3.93 | 3.75 | 3.02 | — | 2.16 |

EXAMPLE 10

Survival of S. liquifaciens sp. 1-102 in Powder Produced by Drying Alginate/Culture Solution

*Serratia liquifaciens* 1-102 was grown as described in Example 1. An aliquot of fresh, healthy *Serratia liquifaciens* 1-102 culture was mixed with 1% sterile non-crosslinked alginate. The resultant mixture was then dried by blowing sterile, filtered air (30° C., liters/min) across the surface of 100 ml. aliquots of the mixture in 4L Erlenmyer flasks. The material obtained was then stored in a sealed container and sampled periodically for viable cell count determination. The results obtained, given in Table 10, show that this composition can be used to maintain viability of *S. liquifaciens* sp. 1-102.

TABLE 10

|  | \multicolumn{5}{c}{Log viable count/g} |
| To | 3 days | 9 days | 15 days | 60 days |
| --- | --- | --- | --- | --- |
| 10.21 | 12.11 | 11.60 | 12.06 | 11.28 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for maintaining a microorganism comprising the steps of:
   (i) selecting a microorganism selected from the group consisting of Serratia, Arthrobacter, Azospirillium, Rhizobium, Bacillus, *Pseudomonas fluorescens* and *Pseudomonas putida* which has a beneficial effect on growth or yield of a plant;
   (ii) providing a solution comprising about 0.01% to about 20% of a substantially soluble, non-crosslinked polysaccharide having no more than about 10% of crosslinking;
   (iii) preparing a suspension of said microorganism;
   (iv) mixing the suspension of the microorganism with the polysaccharide solution to form a pourable composition which, at 4° C.–30° C., is a liquid, said composition comprising from about 0.005% to about 10% by weight of the non-crosslinked polysaccharide; and
   (v) storing the composition.

2. The method of claim 1 wherein said non-crosslinked polysaccharide is alginate.

3. The method of claim 2 wherein said alginate is present in said composition at a concentration of between 0.1–10%.

4. The method of claim 1 further comprising the step of drying said composition before said composition is stored.

5. The method of claim 4 wherein said drying is accomplished by air drying.

6. The method of any of claims 2, 3, 5, 1 or 4 wherein said composition is stored at a temperature of from about 4° C. to about 30° C. for a period of at least one week.

7. A method for inoculating a plant seed with a microorganism comprising the steps of:
   (i) selecting a microorganism selected from the group consisting of Serratia, Arthrobacter, Azospirillium, Rhizobium, Bacillus, *Pseudomonas fluorescens* and *Pseudomonas putida* which has a beneficial effect on growth of yield of a plant;
   (ii) providing a solution comprising about 0.01% to about 20% of a substantially soluble, non-crosslinked polysaccharide having no more than about 10% of crosslinking;
   (iii) preparing a suspension of said microorganism;
   (iv) mixing the suspension of the microorganism with the polysaccharide solution to form a pourable composition which, at 4° C.–30° C., is a liquid, said composition comprising from about 0.005% to about 10% by weight of the non-crosslinked polysaccharide; and
   (v) storing the composition;
   (vi) contacting the plant seed with said composition; and
   (vii) allowing said composition to inoculate the plant seed.

8. The method of claim 7 wherein said non-crosslinked polysaccharide is alginate.

9. The method of claim 8 wherein said alginate is present in said composition at a concentration of between 0.1–10%.

10. The method of claim 7 further comprising the step of drying said composition before said composition is stored.

11. The method of claim 10 wherein said drying is accomplished by air drying.

12. The method of any of claims 8, 9, 11, 7 or 10 wherein said composition is stored at a temperature of from about 4° C. to about 30° C. for a period of at least one week.

* * * * *